United States Patent [19]
Gilcher et al.

[11] 4,385,630
[45] May 31, 1983

[54] BLOOD DONATION UNIT

[75] Inventors: Ronald O. Gilcher, Edmond, Okla.; Allen Latham, Jr., Jamaica Plain, Mass.; Jonathan D. Schiff, Boston, Mass.; Donald W. Schoendorfer, Brookline, Mass.

[73] Assignee: Haemonetics Corporation, Braintree, Mass.

[21] Appl. No.: 182,510

[22] Filed: Aug. 29, 1980

[51] Int. Cl.³ ............................................. A61M 5/00
[52] U.S. Cl. ....................................... 604/31; 604/35; 604/67; 604/151; 604/246
[58] Field of Search ............... 128/275, 214 D, 214 E, 128/214 F, 214 R, DIG. 13, DIG. 14, 214.2, DIG. 12; 417/44, 477; 73/861.25, 736, 703

[56] References Cited

U.S. PATENT DOCUMENTS

| | | | |
|---|---|---|---|
| 1,553,859 | 9/1925 | Hein | 128/214 R |
| 2,406,207 | 8/1946 | Desmet | 128/214 |
| 2,982,286 | 5/1961 | Welch, Jr. | 128/276 |
| 3,095,745 | 7/1963 | Kirwan | 73/736 |
| 3,140,612 | 7/1964 | Houghton et al. | 73/703 |
| 3,339,416 | 9/1967 | Diehl | 73/736 |
| 3,896,803 | 7/1975 | Mason | 128/214 R |
| 3,946,731 | 3/1976 | Liuntenstein | 128/214 E |
| 4,086,924 | 5/1978 | Latham, Jr. | 128/214 R |
| 4,146,172 | 3/1979 | Cullis et al. | 128/214 D |

FOREIGN PATENT DOCUMENTS 2851656 6/1979 Fed. Rep. of Germany ...... 417/477

OTHER PUBLICATIONS

Davol Professional Products Catalog Cut, Providence, Rhode Island, pp. 1-7, 1976.
Cardiovascular Catheters and Accessories, United States Catheter and Instrument Corp. Glens Falls, N.Y. 12801, 1969.
Basic Mechanics of Fluids, Rouse et al., Wiley and Sons, New York, pp. 39-40, 1956.
Catalog Information, SBR Lab., Inc. Elgin, Illinois 60120, 10/79.

*Primary Examiner*—Richard J. Apley
*Assistant Examiner*—J. L. Kruter
*Attorney, Agent, or Firm*—Hamilton, Brook, Smith and Reynolds

[57] ABSTRACT

A blood donation unit in which a reduced outside diameter phlebotomy needle is employed to minimize donor discomfort. The blood flow if, however, maintained at a flow level similar to that obtained with standard gauge phlebotomy needles by a roller pump which provides a predetermined pressure differential between the ends of the phlebotomy needle. The blood is mixed with a predetermined ratio of anticoagulant immediately after passing through the phlebotomy needle. The ratio of whole blood to anticoagulant is independent of the volume of whole blood collected.

9 Claims, 5 Drawing Figures

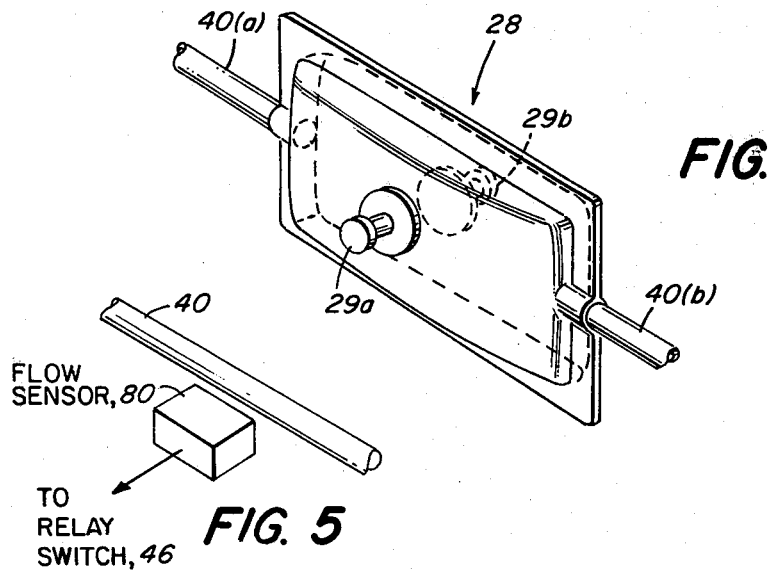
FIG. 3
FIG. 5
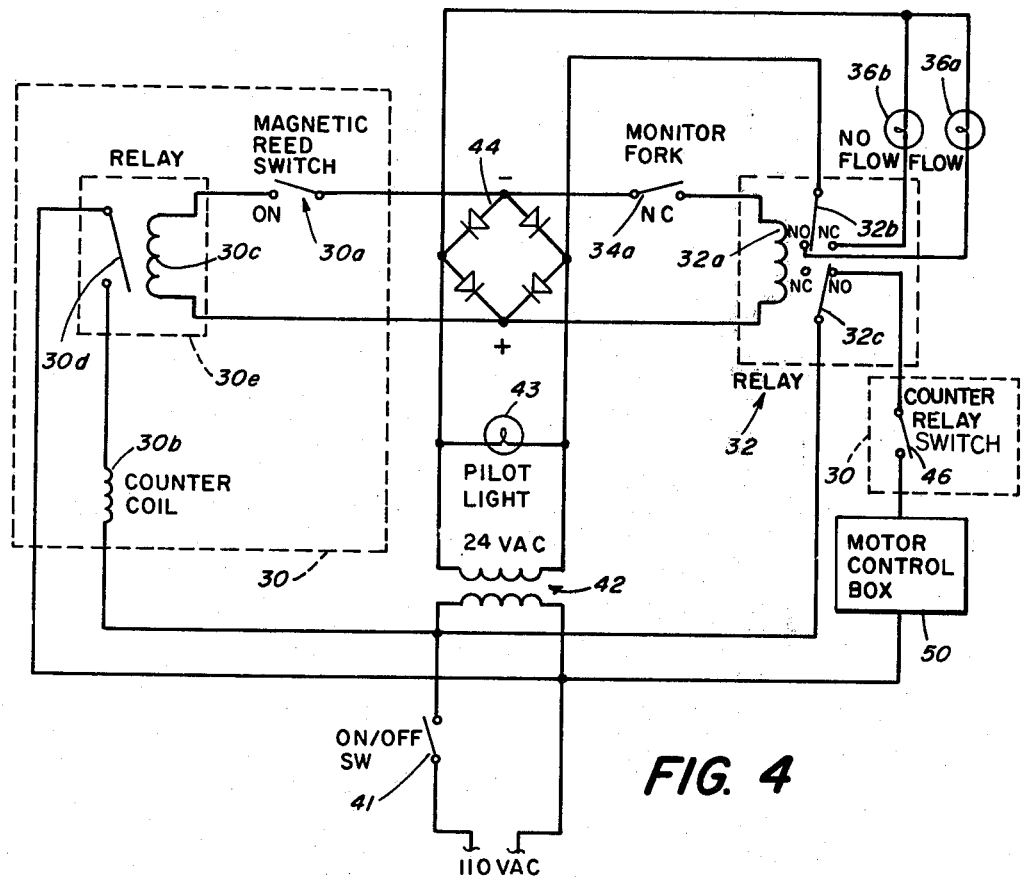
FIG. 4

BLOOD DONATION UNIT

DESCRIPTION

Technical Field

This invention is in the field of blood donation apparatus.

Background Art

In the collection of blood, and more particularly human blood, it is desired that the blood be collected at a controlled rate, such rate to afford minimal physiologic disturbance to the donor and which will preclude damage to the blood cells which would be caused by shearing forces in the event the flow exceeds a certain level. It is also desirable to obtain and store the blood in predetermined volumes and that the collected blood be promptly and completely mixed with anticoagulant solution at specified ratios of blood to anticoagulant so as to minimize damage to the blood.

Conventional systems for collecting blood rely on venouspressure, and hydrostatic pressure to cause blood to flow from a donor's arm. Venouspressure is controllable to some extent by varying the pressure in the cuff attached to the donor's arm above the venipuncture site and by directing the donor to alternately flex and relax his or her hand. Hydrostatic pressure is achieved by positioning the collection bag below the level of the donor's arm, usually about 18" below. This produces a hydrostatic head of about 18" of blood.

In U.S. Pat. No. 2,982,286 to E. S. Welch, Jr., issued on May 2, 1961, there is disclosed a so-called "hemolater" which adds a third controllable source of pressure differential.

The "hemolator" consists of a 500 cc flexible plastic bag which is supplied with 75 cc of anticoagulant. The bag is placed in a rigid chamber. A vacuum between the inside of the chamber and the outside of the bag is created by a vacuum pump causing a negative pressure inside the bag. Blood flows from a donor's vein, which is under a slight positive pressure, through a needle and tube to the bag which is under controlled negative pressure. Means are supplied for agitating the bag while the blood is being drawn and means are also supplied for automatically detecting and measuring the presence of a desired amount of fluid volume in the bag. The rate of flow of blood into the bag is determined by adjustment of a vacuum regulator valve. During the collection of blood, the chamber is continuously pumped and maintained at a level of vacuum as determined by the setting of a screw on the vacuum regulator valve.

In practice, this system has several deficiencies, the most important one being that the flow of blood from the donor is primarily determined by the vacuum set by the set screw in the vacuum regulator valve. The customary 16 gauge size phlebotomy needles were used in this system, and the vacuum regulator could be mistakenly set to produce a vacuum high enough to produce rapid blood flow from the donor which would lead to physiological shock conditions.

With the exception of the "hemolator" as above described, it has become customary within the industry to rely solely on the venouspressure and/or hydrostatic pressure to determine the rate of flow from the donor. It is also customary to utilize a size 16 gauge needle because it is easy to achieve good flow rates with this size needle utilizing solely venouspressure and hydrostatic pressure. However, the 16 gauge needle which has a 0.065 inch outer diameter is a significant deterrent to donor recruitment, due to the pain associated with the venipuncture.

Many of the problems associated with this common technique of whole blood collection stem from the fact that the non-anticoagulated whole blood must pass through the phlebotomy needle and at least 30 inches of tubing before it reaches the anticoagulant in the blood collection bag. If the rate of flow of blood is not maintained at a rapid enough level in the 30 inch section of tubing the activation of clotting factors may occur. When this happens, the clinical usefulness of the blood collection is greatly diminished.

Other problems with the prior art technique are associated with the way the whole blood and the anticoagulant are combined. The amount of anticoagulant which is included in the collection bag is predetermined so that the ratio of final volume of whole blood to anticoagulant is controlled (for example, 7 parts whole blood to one part CPD anticoagulant). However, the first volume of blood that enters the collection bag sees a much greater anticoagulant to whole blood ratio. There is evidence that this transient inflated anticoagulant to whole blood ratio will adversely affect many of the blood components such as Factor VIII and platelet viability. This prior art technique of whole blood collection also requires accurate control of the volume of whole blood collected so that the final whole blood to anticoagulant ratio will be within clinical specifications. This results in a significant wastage of blood due to units of blood that are "overdrawn" or "underdrawn" with respect to the whole blood/anticoagulant ratio.

The American Association of Blood Bank (AABB) publishes guidelines in its Technical Manual (7th Edition) which result in a fairly large percentage of:

(a) rejected drawn units of whole blood for specific clinical applications because a specific volume of whole blood (405 to 495 milliliters) was not collected in less than a specific amount of time (8 minutes);

(b) rejected donors, either because they are less than 110 pounds (unless provisions are available for manually reducing the amount of anticoagulant in the collection bag so that less whole blood can be collected) or because their previous donation experiences have resulted in rejected units.

The AABB also recommends that the blood collection bag be agitated during the collection process as often as every 50 milliliters (ml) of collected blood to insure proper anticoagulant mixing.

The cause for rejection of the above mentioned drawn units of whole blood and potential donors is believed to be inherent in the prior art technique of blood collection.

Accordingly, a need exists for a blood donor system which is sufficiently flexible to accomodate many of the variables recited above and thereby increase the available donor population and which will improve the quality of the drawn blood anticoagulated and stored from presently available donors.

DISCLOSURE OF THE INVENTION

This invention relates to a new and unique blood donor system. In this system, whole blood is withdrawn from a donor using a needle which is between 30%–50% smaller than the outside diameter of the customary size 16 gauge needle. Anticoagulant is introduced and mixed with the whole blood at the outlet of the phlebotomy needle from a tube which is connected to a source of anticoagulant. The anticoagulant tube is passed through a roller pump, the rollers of the pump are in resilient contact with both the outer surface of the anticoagulant tubing and the outer surface of the tubing which serves as a conduit for the anticoagulated blood. Thus, the same pump which controls the flow of the anticoagulant also controls the flow of blood from the donor thereby assuring an accurate ratio of blood to anticoagulant, the ratio being determined by the ratio of the pump tube dimensions and elastic characteristics.

It has been determined that the negative pressure (and, therefore, the rate of flow) through the phlebotomy needle can be increased greatly without compromising the quality of the whole blood components. The roller pump is used to increase the negative pressure in excess of that contributed by the 18" of hydrostatic pressure in the prior art techniques. Thus, for example, it has been found that a normal operating flow rate of 70 ml per minute of donated whole blood can be achieved using venous-pressure and 18" of hydrostatic head and a 16 gauge needle. A standard collection volume of whole blood is about 450 ml which under normal processing (i.e., venouspressure and hydrostatic head only) would take approximately six to eight minutes. Using the apparatus of the present invention, a 19 or 20 gauge needle is substituted for the standard 16 gauge phlebotomy needle and a negative pressure can be established equivalent to a hydrostatic head of about 66" of water which results in a collection of 450 ml of whole blood in about the same amount of time. However, this collection is accomplished using a smaller phlebotomy needle size which results in far less pain and trauma to the donor.

In addition, since the same pump is used to meter the anticoagulant into the tubing with the donated whole blood, an accurate ratio of anticoagulant mixing is continually achieved. Mixing of anticoagulant and blood in the correct ratio is performed immediately downstream from the needle at a Y-junction, and thus damage to the blood from anticoagulant shock is avoided and periodic agitation of the collection bag is not necessary.

Furthermore, in order to avoid collapsing of the vein in the event the vacuum is such that more blood is withdrawn from the donor than the vein can accomodate, sensing means are provided in the apparatus of the present invention which will automatically slow or stop the pump when the pressure goes below a certain level or when the rate of flow drops below a certain level.

The ratio of whole blood to anticoagulant is constant throughout the collection. Therefore, the time for collection is no longer an important concern, as there is no lag in the anticoagulation. Also, the collection can be terminated at any time and still preserve full clinical usefulness of the blood—as the anticoagulant to whole blood ratio is not a function of the volume of blood collected. Thus, "overdrawn" and "underdrawn" units of blood are eliminated resulting in more usable units of blood.

BRIEF DESCRIPTION OF THE DRAWINGS

FIG. 3 is a perspective showing the details of the pressure bag 28 of FIG. 1;

FIG. 4 is a schematic diagram of the electronics associated with the apparatus of FIGS. 1 and 2.

FIG. 5 is a schematic diagram illustrating a non-invasive flow meter embodiment of the invention.

BEST MODE OF CARRYING OUT THE INVENTION

Figure 1:
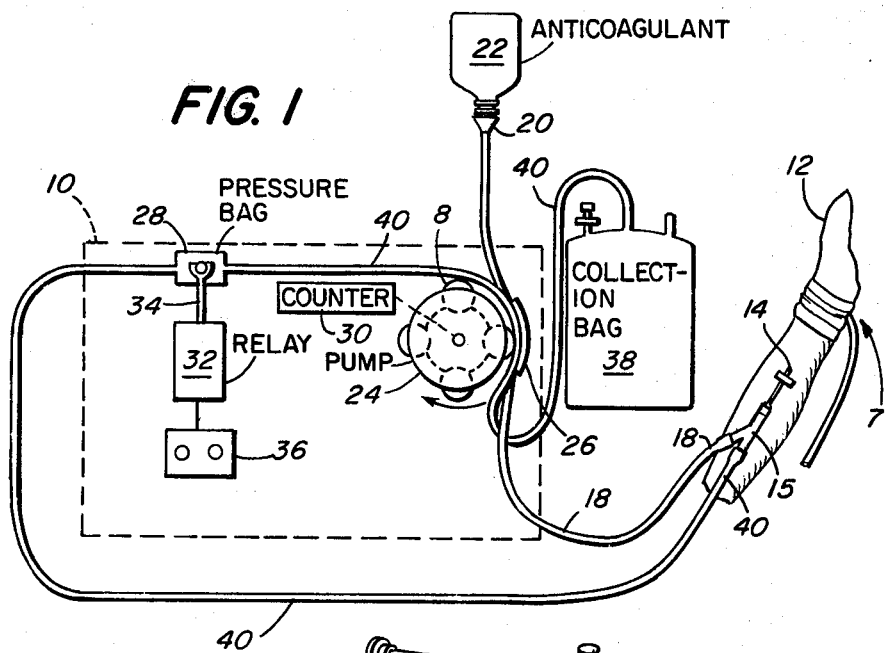
FIG. 1 is a diagrammatic illustration of a blood donor system of this invention.
Figure 2:
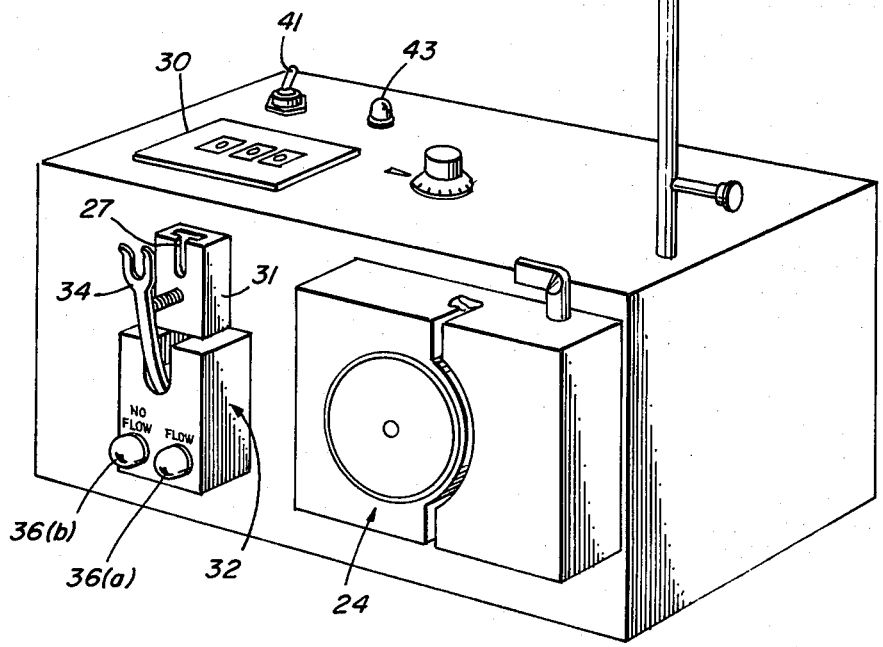
FIG. 2 is a perspective of the mechanical configuration of the invention.

The preferred embodiment of this invention can be described in more detail with reference to FIG. 1 which illustrates a suitable blood donor system 10 together with a blood donor's arm 12. A reduced diameter phlebotomy needle 14 is used in this apparatus. Phlebotomy needle 14 is preferably a 19 gauge×1.5 inch thin wall needle of the type which has a supply of anticoagulant connected to it at a Y-junction 15 so that freshly withdrawn blood is anticoagulated at this Y-junction as soon as it leaves the needle. One specific type of phlebotomy needle is described in detail in issued U.S. Pat. No. 3,916,892 to Latham.

A size 19 gauge thin wall needle has an outer diameter (OD) of 0.042 inches and an inner diameter (ID) of 0.031 inches. This can be compared with the customary use of size 16 gauge needles with ID's of 0.047 and OD's of 0.065. The needle size reduction afforded by this invention significantly reduces physiologic effects and as will be explained later is accomplished without deleterious side effects otherwise usually associated with a reduction in ID and OD of needle size, such as, unacceptably long blood withdrawal times and blood cell shearing damage caused by excessive flow rates being applied to the blood as it is withdrawn.

Anticoagulant is supplied to a phlebotomy needle 14 through tubing 18 which may be connected through a sight drip 20 to pouch 22 containing anticoagulant. The other end of tubing 18 is connected to the phlebotomy needle 14 through Y-connector 15, to which is also connected tubing 40. Tubing 40 is the conduit for the anticoagulated whole blood being withdrawn from the donor's arm 12.

A pump 24 is provided of the type described in detail in U.S. Pat. No. 3,565,286. Pump 24 is a roller type pump having a movable platen 26 which clamps tubing 18 against the rollers 8 of pump 24 when it is in its closed position. As will be explained in detail later tubing 40 containing the whole blood withdrawn from the donor and mixed with anticoagulant is also clamped against the same rollers by platen 26.

Prior to making the venipuncture, phlebotomy needle 16 may be primed with anticoagulant by opening platen 26 so that the stationary rollers 8 of anticoagulant pump 24 do not restrict the flow in tube 18. With platen 26 in the open position, the outlet of anticoagulant pouch 22 is opened without interfering with the sterility of the system, usually by displacing a small round ball at its neck using mere thumb pressure. After a small amount of anticoagulant flows into sight-drip 20, it is manually squeezed in a manner which expresses air into anticoagulant pouch 22 and thereafter provides a small reservoir of anticoagulant in sight-drip 20. Anticoagulant flow is allowed to continue until all air has been displaced from tube 18 and needle 14. The maintenance of the small reservoir of anticoagulant in the sight-drip 20 and the ability to observe the anticoagulant flow during the procedure provides visual assurance to operators that anticoagulant is flowing into the system. However, it may be dispensed with without substantially affecting the integrity of the system.

The site where the venipuncture is to be made is then prepared. After that, if desired, a conventional pressure cuff 7 is fastened around the donor's arm 12 at a location above where phlebotomy needle 14 is to be inserted. A typical pressure is about 40 mm of mercury which raises the pressure in a donor's veins sufficiently to facilitate the venipuncture and to boost blood flow from the donor's veins. As an option in design, a cuff pressure pump, control system, and pressure cuff would be included as part of the donor system 10 (not shown). In this case, the pressure cuff 7 would be automatically controlled by the logic in the system.

Pump platen 26 is then closed thereby clamping tube 18 and 40 into pump 24. At this point, the venipuncture is made by inserting the phlebotomy needle 14 into one of the donor's veins at the previously prepared site. The pump 24 is then turned on. Freshly withdrawn whole blood flows from the donor, mixes with the ratioed anticoagulant at Y-junction 15 and flows through tubing 40 into pressure bag 28.

Pressure bag 28, as more clearly shown in FIG. 3, is a plastic bag with a pair of plastic ribs or buttons 29a and 29b attached to each side. Arm 34 of relay switch 32 is inserted under the rib 29a between the outer surface of the bag and the flange surface of the rib. Rib 29b slides on the slot 27 provided on the housing for relay switch 32. As long as there is adequate blood flow into pressure bag 28 to keep it expanded relay switch 32, as will be more fully explained in connection with FIG. 4, will be activated and in turn switch the pump 24 on. Relay switch 32 will also activate the "Flow" light 36a to show the donor and phlebotomist that the device is working properly. Anticoagulated whole blood then passes further along through tube 40b where it is disposed between the pump rollers 27 and movable platen 26 of pump 24. The platen clamps tubing 40 against the rollers of pump 24 when it is in its closed position. Tubing 40, after passing through pump 24, is connected to collection bag 38. Tubing 40 consists of blood tubing of 0.120 ID×0.170 OD inches diameter. Tubing 18 is anticoagulant tubing of 0.039 ID×0.090 OD inches in diameter. Collection bag 38 is a 600 ml collection bag.

Under normal operating conditions and using a size 19 guage thin wall needle, pump 24 is operated at a speed which will create a vacuum of about 65.8" of water. As will be explained below, this is sufficient to create a flow of approximately 70 ml per minute of blood through the size 19 gauge thin wall needle. A flow of 70 ml is the rate of flow normally created through a 16 gauge needle without a vacuum and relying solely on venapressure and hydrostatic head. Thus, insofar as the donor is concerned, his or her physiologic reaction is the same as it would be had an ordinary venipuncture occurred except that a much smaller size needle is employed which will cause less trauma and physiologic reaction.

The flow of blood Q in cm$^3$/minute from the donor side of the phlebotomy needle to the pump side is governed to a first order approximation in low Reynold's number flow by the Hagen-Poiseulle Formula as follows:

$$Q = \Delta P(\pi R^4 / 8 \mu L)$$

wherein:

$\Delta P$ is the pressure drop across the needle in grams per cm-sec$^2$;

R is the inner radius of the needle in cm;

$\mu$ is the viscosity of the medium in gm/cm-sec; and

L is the length of the needle in cm.

Assuming a desirable flow rate of 70 ml per minute, and a size 19 gauge thin wall needle 1.5 inches long and a viscosity of 0.035 gm/cm-sec for blood of 45% hematocrit; $\Delta P$ is substantially 65.8" of water.

There is also provided in accordance with the invention apparatus for preventing the collapse of a vein in the event that more blood is being pulled through the system than the vein can accommodate. Thus, in the event the flow of blood tends to decrease, as would occur when the vein starts to collapse, the pressure bag 28 will also tend to collapse causing relay arm 34 to move inwardly (away from the viewer in FIG. 1) deactivating relay switch 32 which turns off pump 24 and simultaneously lights the "no flow" light 36b alerting the operator to the fact that the flow of blood has ceased. It is also contemplated that, rather than waiting for blood to stop flowing completely the relay switch mechanism can be adjusted to turn the pump off and activate the "no flow" light when the flow of blood is less than some other predetermined level. It is further contemplated that instead of shutting completely off with a low-flow signal from relay 32, the pump could be made to continue to pump, but at a much slower rate. This would maintain some flow of blood through the needle and so prevent stasis of blood in the phlebotomy needle.

Alternatively, in lieu of the bag 28 which is responsive to pressure in the tubing, a non-invasive flow meter such as ultrasonic flow meter 80 as shown in FIG. 5 could be substituted and used to sense the flow of blood through the tubing 40. In the event the flow is stopped or is less than a predetermined level a signal from the flow meter 80 would deactivate the pump and light the "no flow" light 36b. A donor would be coached to flex and relax his fist to increase venous flow once the donor sees the "no flow" light indicating the flow is low. This will significantly reduce the chances of clotting which may occur in the smaller size needle when flow of blood is completely stopped.

Referring now to FIG. 4 the details of the electronic circuitry will be described. Line voltage of 110 volts AC 60 cycles is coupled through the "ON" position of switch 41 to step-down transformer 42. Transformer 42 converts the 110 volts AC to 24 volts AC. Pilot light 43 is in parallel with the secondary of transformer 42. The 24 volts AC is coupled across rectifier 44 where it is rectified into 24 volts DC. The 24 volts DC is coupled to the windings 32a and 30c of two control relays, 32 and 30 through respective switches monitor fork switch 34a and magnetic reed switch 30a.

Relay winding 30c which is located within counter 30 controls the operation of contact 30d. Counter 30 consists of a magnetic reed switch 30a, a relay 30e and a counter coil 30b.

The counter operates as follows: As the pump 24 rotates, a magnet (not shown) imbedded in the pump rotor head flips the magnetic reed switch 30a to the ON position once per revolution, which in turn energizes the coil 30b in the counter circuit, by applying a 24 volt DC signal across winding 30c which closes the contact 30d which thereby allows the 120 volts AC line voltage to pass to the coil 30b of the counter circuit. Every time the counter coil receives an impulse of 120 volts, it counts off one more digit. In other words once per revolution, the magnetic reed switch 30a closes which activates the relay 30e which allows the counter coil circuit to be completed. The counter itself (not shown) is a well-known device which has an electromagnetic coil in it which, when activated, pulls down a cam which is in contact with a rotatable set of numeric indicia. All the digits in the counter have teeth which are rotated by the cams.

One revolution of the pump rotor corresponds to withdrawal of approximately 1 ml of blood, accordingly if it is desired to withdraw 450 ml of blood the counter is initially set at 450 and counts down until the cam in the counter no longer has any opposing teeth to come down upon because it is at zero. When the count reaches zero, switch 46, which connects line voltage to the motor control box is opened and so no power reaches the motor and the motor stops. Alternatively, the counter will start at zero and count up the number of revolutions, approximately equivalent to the number of milliliters of whole blood collected, until the count reaches a preset number (e.g. 450), at which point the pump would be turned off as described above.

The monitor circuit operates as follows: With blood flowing the monitor fork switch 34a is closed by the pressure bag 28. Thus the windings 32a of relay 32 are energized placing contact 32b in the position shown in FIG. 4, thereby completing the 24 volt DC path to flow light 36a. Also, when coil 32a is energized, switch 32c is placed in the position shown in FIG. 4 so as to provide line voltage to motor control box 50.

As soon as the monitor fork switch 34a is opened, such as, by the pressure bag 28 collapsing when blood stops flowing for any reason; coil 32a is de-energized, switch contact 32b moves to the position opposite that shown in FIG. 4 and energizes "no flow" light 36b. At the same time switch contact 32c moves to the position opposite that shown in FIG. 4 thus breaking the circuit to motor control box 50 and de-energizing the pump 24. This completes the description of the electronic circuit of FIG. 4.

It should be noted that an advantage of utilizing one pump 24 for pumping both the anticoagulant and the whole blood is that a closed loop is thereby established so that once the pressure bag collapses no more fluid will be pumped through either line. Thus, if, for example, the needle became blocked so that the flow of blood from the donor is stopped, the pressure bag will collapse even though anticoagulant flow may continue for a while since the pump is trying to take out a flow several times greater than the flow of anticoagulant from the bag; and the pump will be turned off. When not rotating, the pump acts as a stop valve.

EQUIVALENTS

Those skilled in the art will recognize many equivalents to the specific embodiments described herein. Such equivalents are part of this invention and are intended to be covered by the following claims.

What is claimed is:

1. A blood donor collection system wherein blood is withdrawn from a donor under negative pressure created by a pump means, said system comprising: a pump means, a phlebotomy needle, said needle having a length L (in centimeters) and an inner radius R (in centimeters), said needle also having a first end insertable into said donor and a second end coupled to junction means, said junction means joining said needle with both a first end of first conduit means and a first end of second conduit means, said first conduit means having a second end thereof connected to a whole blood collection bag and said second conduit means having a second end thereof connected to a bag at least partially containing anticoagulant, said pump means being disposed to achieve a flow rate Q of blood at least on the order of 70 ml per minute by maintaining an essentially constant negative pressure differential $\Delta P$ of at least about 168 cm of water across the length L of the interior of said needle, said flow rate Q governed to a first order approximation in low Reynold's number flow by the Hagen-Poiseulle Formula:

$$Q = \Delta P \pi R^4 / 8 \mu L$$

where $\mu$ is the viscosity of blood (in gram/cm-sec).

2. The apparatus of claim 1 wherein R is no greater than about 0.015 cm, L is about 3.8 cm, and $\mu$ is about 0.035 gm/cm-sec.

3. The apparatus of claim 1 in which sensing means are provided in association with said first conduit means which will deactivate the pump means when fluid passing through said first conduit means fails to attain a predetermined pressure level.

4. The apparatus of claim 1, wherein said pump means causes anticoagulant to be pumped from said source of anticoagulant through said second conduit means and into said junction means where said anticoagulant is mixed in a predetermined volumetric ratio with said blood withdrawn from said donor while said pressure differential $\Delta P$ is maintained substantially constant across the length L of the interior of said needle; and wherein said apparatus further comprises means for deactivating said pump means when said pressure differential substantially changes.

5. The apparatus of claim 4 including pump revolution counter means for deactivating said pump means after a predetermined number of counts.

6. The apparatus of claim 4 wherein the pump means comprises a single rotary peristaltic pump with rollers and a platen and wherein the conduit means is disposed between the rollers and the platen.

7. The apparatus of claim 4 which includes indicator means to notify the donor when the pump is deactivated so that the donor will flex and relax his fist to increase venous blood flow.

8. The apparatus of claim 4 including means to deactivate said pumping means once a predetermined volume of whole blood has been collected.

9. The apparatus of claim 4 in which the sensing means for deactivating said pump means measures the rate of flow of blood in said first conduit means.

* * * * *